United States Patent
Inoue et al.

(10) Patent No.: US 9,094,596 B2
(45) Date of Patent: Jul. 28, 2015

(54) IMAGE PICKUP SYSTEM HAVING IMAGE QUALITY IMPROVING FUNCTION OF IMAGE PICKUP SIGNAL

(71) Applicants: NEC CORPORATION, Minato-ku, Tokyo (JP); Nippon Avionics Co., Ltd., Shinagawa-ku, Tokyo (JP)

(72) Inventors: Kazunori Inoue, Tokyo (JP); Shuichi Ohkubo, Tokyo (JP)

(73) Assignees: NEC CORPORATION, Tokyo (JP); NIPPON AVIONICS CO., LTD., Tokyo (JP)

( * ) Notice: Subject to any disclaimer, the term of this patent is extended or adjusted under 35 U.S.C. 154(b) by 152 days.

(21) Appl. No.: 13/763,053

(22) Filed: Feb. 8, 2013

(65) Prior Publication Data

US 2013/0208142 A1     Aug. 15, 2013

(30) Foreign Application Priority Data

Feb. 10, 2012   (JP) ................. 2012-026876

(51) Int. Cl.
*H04N 5/225*     (2006.01)
*G01N 21/3581*   (2014.01)

(52) U.S. Cl.
CPC ......... *H04N 5/2256* (2013.01); *G01N 21/3581* (2013.01)

(58) Field of Classification Search
CPC ..... H04N 1/2112; H04N 5/772; H04N 5/907; H04N 2101/00; H04N 1/2158
USPC ...................................... 348/231.7
See application file for complete search history.

(56) References Cited

U.S. PATENT DOCUMENTS

| 5,598,145 | A | 1/1997 | Shimotani et al. |
| 7,851,761 | B2 * | 12/2010 | Popa-Simil ................ 250/341.1 |
| 8,159,667 | B2 * | 4/2012 | Kukushkin et al. ........... 356/326 |
| 8,772,890 | B2 * | 7/2014 | Kukushkin et al. ........... 257/428 |
| 2002/0005951 | A1 * | 1/2002 | Fukasawa .................... 356/432 |
| 2009/0116707 | A1 * | 5/2009 | Sutko et al. ................... 382/128 |

FOREIGN PATENT DOCUMENTS

| JP | 07-134800 A | 5/1995 |
| JP | 2002-232907 A | 8/2002 |
| JP | 2003-208599 A | 7/2003 |

\* cited by examiner

*Primary Examiner* — Twyler Haskins
*Assistant Examiner* — Fayez Bhuiyan
(74) *Attorney, Agent, or Firm* — Sughrue Mion, PLLC

(57) ABSTRACT

A camera generates a light source control signal for controlling a light source to turn the light source on and off, acquires a plurality of items of first image data and a plurality of items of second image data obtained by picking up the measured wave, and transfers the plurality of items of acquired first image data and the plurality of items of acquired second image data to an external storage and processing device as digital data with an identifying number for identifying a frame in which the image data is acquired attached every frame. The external storage and processing device determines whether each frame of the digital data is an item of the first image data or an item of the second image data on the basis of the identifying number, and subtracts the plurality of items of determined second image data from the plurality of items of determined first image data to produce difference image data.

10 Claims, 6 Drawing Sheets

RELATED ART

FIG. 1

RELATED ART

FIG. 2

RELATED ART

FIG. 3

RELATED ART

RELATED ART

FIG. 12

IMAGE PICKUP SYSTEM HAVING IMAGE QUALITY IMPROVING FUNCTION OF IMAGE PICKUP SIGNAL

This application is based upon and claims the benefit of priority from Japanese patent application No. 2012-026876, filed on Feb. 10, 2012, the disclosure of which is incorporated herein in its entirety by reference.

BACKGROUND OF THE INVENTION

1. Field of the Invention

This invention relates to an image pickup system comprising a light source, a camera, and a measured target located in an optical path therebetween and, more particularly, to a lock-in image pickup system for performing imaging by bringing a period of turning-on/off of the light source into sync with a frame of the camera.

2. Description of Related Art

As an image pickup system, a THz image pickup system in a terahertz (THz) frequency range is known.

A terahertz wave (a THz wave) refers to an electromagnetic wave having frequencies of about 0.1 to 10 THz (wavelengths of 3000 μm to 30 μm). That is, the terahertz wave (the THz wave) has wavelengths located between micro wave and an infrared, and is called a submillimeter wave. It is known that the terahertz wave (the THz wave) easily passes through nonconductive (nonmetal) materials such as papers (paper products), plastic, cloth (clothing), vinyl, ceramics, lumber, bones, teeth, fat, powder, dried foods, walls, or the like and nonpolarized materials. Therefore, for example, the terahertz wave (the THz wave) can be used to detect metallic or nonmetallic arms hided in the manner which is almost similar to a case where an X-ray is currently used to security in airport.

Inasmuch as the terahertz wave (the THz wave) easily passes through the papers (the paper products) in the manner which is described above, the terahertz wave (the THz wave) may be applicable, for example, to detect contents in an envelope without opening the envelope.

Figure 1:
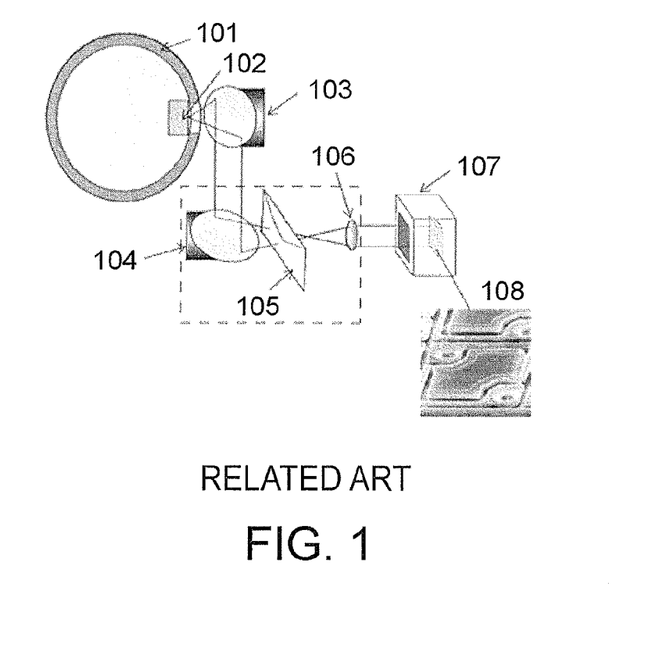
FIG. 1 is a view showing configuration of a related terahertz image pickup system.

Referring now to FIG. 1, the description will proceed to a related terahertz image pickup system. The related terahertz image pickup system comprises a refrigerator 101, a quantum cascade laser 102, a first off-axis parabolic mirror 103, a second off-axis parabolic mirror 104, a target (a measured target) 105, a Si lens 106, an a micro bolometer camera 107 containing a (320×240) pixel micro bolometer array sensor 108. The example being illustrated shows a case where the target (the measured target) 105 comprises an envelope.

The quantum cascade laser 102 is contained in the refrigerator 101. The quantum cascade laser 102 serves as a THz light source and radiates an emission line (a THz wave) having a frequency of 3.1 THz. Radiated from the quantum cascade laser 102, the emission line (the THz wave) is reflected by the first off-axis parabolic mirror 103 and the second off-axis parabolic mirror 104 and passes through the target (the envelope) 105. Passed through the target (the envelope) 105, the THz wave is subjected to a parallel THz wave by the Si lens 106, and is picked up by the micro bolometer camera 107 to obtain a THz transmission image.

Figure 2:
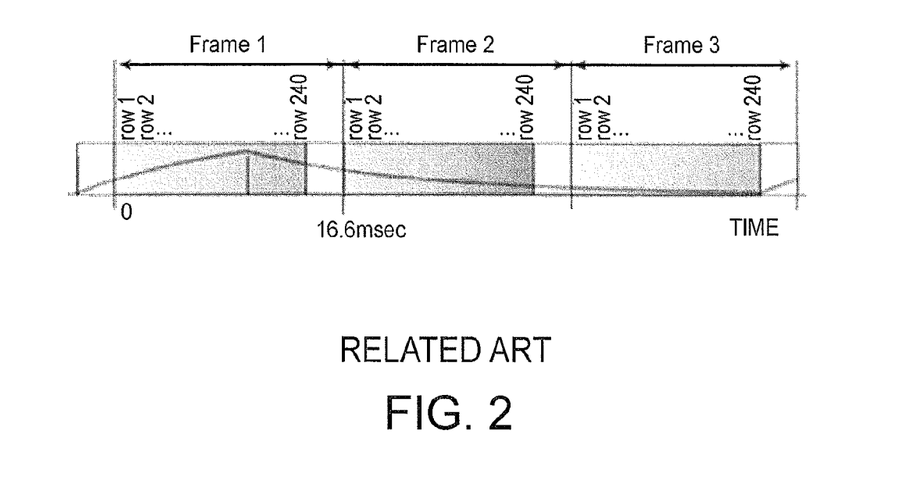
FIG. 2 is a view showing a method of acquiring a difference image in the related terahertz image pickup system.

FIG. 2 show a view showing a method of acquiring a difference image in the related terahertz image pickup system illustrated in FIG. 1.

Figure 3:
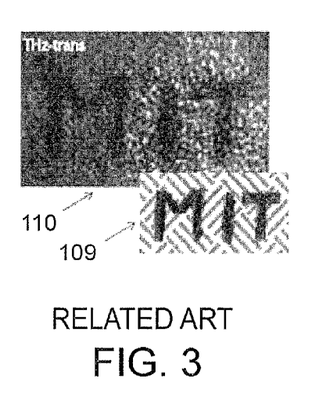
FIG. 3 is a view showing a THz transmission image acquired from a subject (an envelope in which a paper with a letter of MIT written with a pencil is entered) by using the related terahertz image pickup system.

FIG. 3 shows the THz transmission image acquired by using the related terahertz image pickup system illustrated in FIG. 1. In FIG. 3, a reference numeral of 109 indicates a paper on which a letter of MIT is written with a pencil, and a reference numeral of 110 indicates the THz transmission image obtained by picking up the paper 109 put in the envelope 105.

Various prior art documents related to this invention are already known.

By way of illustration, JP 07-134800 A (which will later be called Patent Document 1 and which corresponds to U.S. Pat. No. 5,598,145) discloses a "driver image pickup device" in which a face image according to infrared radiation LED illuminating light only can be obtained by subtracting an "image according to extraneous light" from an "image according to the extraneous light plus LED turned on" in order to omit influence of the extraneous light.

In addition, JP 2003-208599 A (which will later be called Patent Document 2) discloses an "object recognition device" comprising: comparing an image in a case of turning on a luminaire with an image a case of turning out the luminaire; extracting information due to the luminaire alone from a difference therebetween; and creating an image corresponding to one picked up under a illumination condition within a constant range.

Furthermore, JP 2002-232907 A (which will later be called Patent Document 3) discloses a "digital image pickup device" comprising: subtracting, from first image data obtained on turning on a flash, second image data obtained on turning off the flash to calculate difference image data; and calculating, as illumination component data, data indicative of influence where an illumination environment to a subject provides to the image on the basis of the first image data, the second image data, the difference image data, and flash spectroscopic data. In the digital image pickup device disclosed in Patent Document 3, it is possible to further calculate suitable illumination component data and object color component data by obtaining plural set of the first images and the second images with exposure conditions such as a shutter speed, an iris value, and so on changed.

Inasmuch as the conventional examples disclosed in Patent Documents 1-3 calculate a difference image between one frame image upon turning on the light source and one frame image upon turning off the light source, it is disadvantageous in that image quality (a signal-to-noise ratio) is not as improved as one expected. This is because fixed background noises are removed by calculating the difference image but it is impossible to remove random noises.

In order to further improve the image quality, it is effective to a method of obtaining a plurality of frames including image data upon turning on the light source and image data upon turning off the light source, and carrying out average processing on the plurality of items of image data to decrease the random noises, as described in Patent Document 3. However, in a case where an operation processing is carried out by capturing the image data of the plurality of frames into an external storage and processing device such as a personal computer, it is feared that the image data is loss by failing the capturing.

Figure 4:
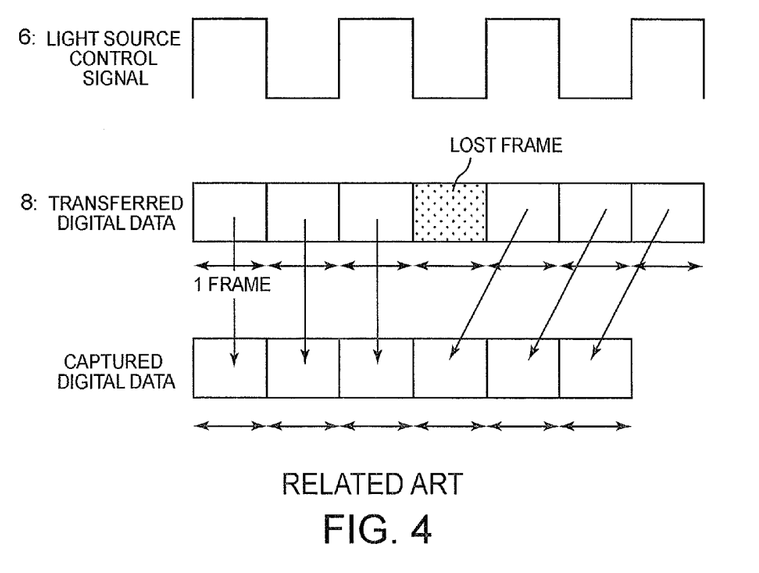
FIG. 4 is a view for use in describing a situation where a part of digital data transferred to an external storage and processing device is lost.

In this event, as shown in FIG. 4, the image data of the frame upon turning on the light source may be erroneously used as the image data of the frame upon turning off the light source or the image data of the frame upon turning off the light source may be erroneously used as the image data of the frame upon turning on the light source. It is therefore disadvantageous in that the image quality is not improved although the average processing is carried out.

It may be considered to a method of carrying out the average processing by estimating whether captured image data corresponds to the frame upon turning on the light source or to the frame upon turning off the light source after capturing all of the image date into the external storage and processing device. However, this method is disadvantageous in that a time is consumed on the data processing and is disadvantageous in that the image quality is not improved in a case where the image quality is low because the accuracy of estimating becomes low.

Furthermore, when a sensor embedded in the camera has a large time constant, it is impossible to acquire stable image data at frames immediately after switching from turning-off of the light source to turning-on thereof or switching from turning-off of the light source to turning-off thereof. It is therefore impossible to improve the image quality except in cases where the average calculation is carried out by excluding the image data corresponding to those frames. However, it is difficult to accurately estimate whether or not those image date correspond to the frames immediately after switching turning-on/off of the light source after the image data are captured.

SUMMARY

It is an object of the present invention to improve image quality by certainly determining, as regards image data of a plurality of frames, image data of the frames upon turning on a light source and image data of the frames upon turning off the light source in a short time and by carrying out lock-in operation and average operation.

In one embodiment, there is provided an image pickup system including a light source radiating an electromagnetic wave, a camera picking up a measured wave into which the electromagnetic wave transmits a measured target or reflects from the measured target to obtain image data, and an external storage and processing device connected to said camera. The camera includes light source control means generating a light source control signal for controlling the light source to turn the light source on and off, image acquisition means acquiring a plurality of items of first image data obtained by picking up the measured wave upon turning on the light source and a plurality of items of second image data obtained by picking up the measured wave upon turning off the light source to produce a plurality of items of acquired first image data and a plurality of items of acquired second image data, and data transferring means transferring the plurality of items of acquired first image data and the plurality of items of acquired second image data to the external storage and processing device as digital data with an identifying number for identifying a frame in which the image data is acquired attached every frame. The external storage and processing device includes data determining means determining, on the basis of the identifying number, whether each frame of the digital data is an item of the first image data or an item of the second image data to produce a plurality of items of determined first image data and a plurality of items of determined second image data, and subtracting means subtracting the plurality of items of determined second image data from the plurality of items of determined first image data to produce difference image data.

BRIEF DESCRIPTION OF THE DRAWINGS

The above features and advantages of the present invention will be more apparent from the following description of certain preferred embodiments taken in conjunction with the accompanying drawings, in which.

DETAILED DESCRIPTION OF EXEMPLARY EMBODIMENTS

The invention will be now described herein with reference to illustrative embodiments. Those skilled in the art will recognize that many alternative embodiments can be accomplished using the teachings of the present invention and that the invention is not limited to the embodiments illustrated for explanatory purposes.

Now, the description will be made as regards a summary of this invention.

An image pickup system according to a first aspect of this invention comprises an image pickup system which comprises a light source, a camera, and a measured target located therebetween. The camera has a function for generating a light source control signal for controlling the light source and a function for transferring digital data to an external storage and processing device. The digital data includes image data picked up by the camera and an identifying number for identifying a frame in which the image data is acquired. The identifying number roundly changes at a predetermined period. It will be assumed that the identifying number has a maximum number of $N_{max}$ and a minimum number of $N_{min}$, the camera has a synchronous signal having a frequency of $F_S$, and the light source control signal has a frequency of $F_L$. In this event, $N_{max}$, $N_{min}$, $F_S$, and $F_L$ are satisfied with the following expression:

$$1 \le (N_{max} - N_{min}) \le (F_S/F_L).$$

In addition, an image pickup system according to a second aspect of this invention comprises an image pickup system which comprises a light source, a camera, and a measured target located therebetween. The camera has a function for generating a light source control signal for controlling the light source and a function for transferring digital data to an external storage and processing device. The digital data includes image data picked up by the camera and an identifying number for identifying a frame in which the image data is acquired. The camera transfers, to the external storage and processing device, the identifying number twice or more prior to the image data in question.

A lock-in image pickup system according to a third aspect of this invention comprises a light source, a camera, a measured target located between the light source and the camera, and an external storage and processing unit. The camera has a function for transferring, to the external storage and processing unit, image data and an identifying number which roundly changes at a predetermined period and a function for generating a light source control signal for controlling the light source. The external storage and processing device has an operation function for determining, on the basis of the identifying number, whether the image data comprises image data acquired in the frame when the light source turns on or image data acquired in the frame when the light source turns off and for subtracting the image data acquired in frames when the light source turns off from the image data acquired in the frames when the light source turns on. It will be assumed that the identifying number has a maximum number of $N_{max}$ and a minimum number of $N_{min}$, the camera has a synchronous signal having a frequency of $F_S$, and the light source control signal has a frequency of $F_L$. In this event, $N_{max}$, $N_{min}$, $F_S$, and $F_L$ are satisfied with the following expression:

$$1 \le (N_{max} - N_{min}) \le (F_S/F_L).$$

Furthermore, a lock-in image pickup system according to a fourth aspect of this invention comprises a light source, a camera, a measured target located between the light source and the camera, and an external storage and processing unit. The camera has a function for generating a light source control signal for controlling the light source and a function for transferring digital data to the external storage and processing unit. The digital data includes image data picked up by the camera and an identifying number for identifying a frame in which the image data is acquired. The camera has a function for transferring, to the external storage and processing device, the identifying number twice or more prior to the image data in question. The external storage and processing device has an operation function for subtracting, on the basis of the identifying number, the image data acquired in frames when the light source turns off from the image data acquired in the frames when the light source turns on. The external storage and processing device determines the identifying number by reading out the identifying number twice or more within one frame.

The description will proceed to an exemplary embodiment of this invention with reference to drawings in detail.

Figure 5:
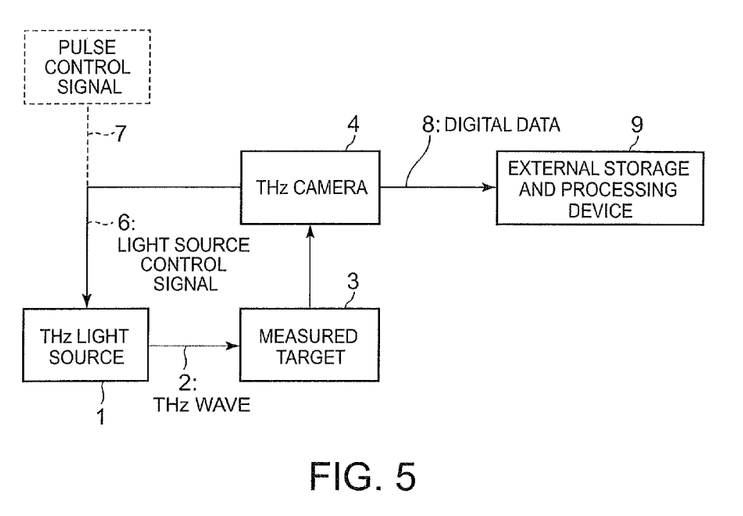
FIG. 5 is a view showing en example of configuration of a lock-in image pickup system according to an exemplary embodiment of this invention.

Referring to FIG. 5, an image pickup system according to the exemplary embodiment of this invention comprises a THz light source 1 for radiating a THz wave 2 as an electromagnetic wave, a measured target 3, a THz camera 4, and an external storage and processing device 9. The measured target 3 is located in an optical path between the THz light source 1 and the THz camera 4.

Emitted (Radiated) from the THz light source 1, the THz wave 2 is irradiated to the measured target 3 and is detected (picked up) by the THz camera 4 as a reflected wave or a transmitted wave. Herein, the reflected wave and the transmitted wave will be collectively called a measured wave. In the exemplary embodiment, the description will later proceed as an arrangement of reflection.

Figure 6:
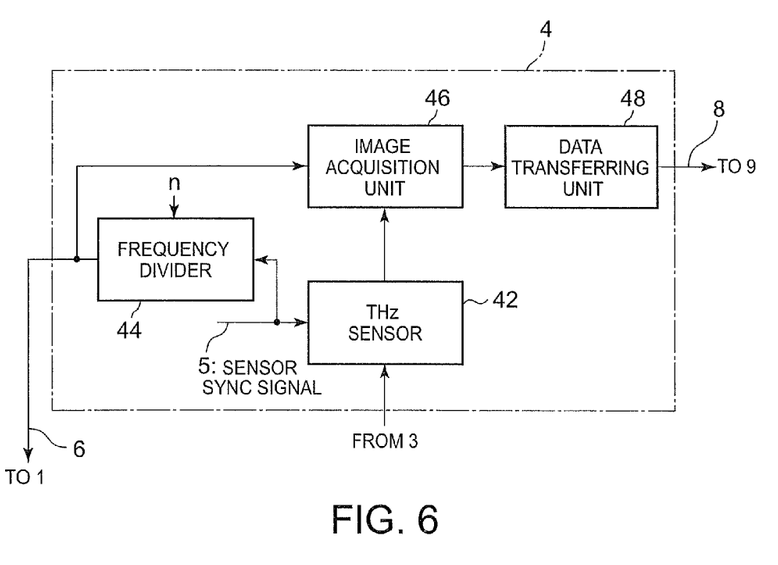
FIG. 6 is a block diagram of a THz camera for use in the lock-in image pickup system illustrated in FIG. 5.

As shown in FIG. 6, the THz camera 4 includes a THz sensor 42 and a frequency divider 44. The THz sensor 42 is supplied with a sensor synchronous signal 5. The sensor synchronous signal 5 is supplied to the frequency divider 44. The frequency divider 44 is also supplied with a dividing number n, where n represents a positive integer. The frequency divider 44 frequency divides the sensor synchronous signal 5 on the basis of the dividing number n to produce a divided signal. The divided signal is supplied to the THz light source 1 as a light source control signal 6. Accordingly, the frequency divider 44 serves as light source control means which generates the light source control signal 6 for controlling the THz light source 1 to turn the THz light source 1 on and off.

In a case where it is difficult that the THz light source 1 makes DC emission, the THz light source 1 is supplied with a control signal obtained by ANDing the light source control signal 6 and a pulse control signal 7. Inasmuch as the pulse control signal 7 has a repetition frequency of, for example, 1 kHz that is sufficiently faster as compared with a time constant (of about 16 msec) of the THz sensor 42, it is possible to consider that DC light having average power is irradiated during the light source control signal 6 takes ON (H level).

Acquired by the THz camera 4, image data is captured to the external storage and processing device 9 as digital data together with an identifying number for identifying a frame in which the image data in question is acquired.

Accordingly, as shown in FIG. 6, the THz camera 4 comprises an image acquisition unit 46 for acquiring a plurality of items of first image data obtained by picking up the measured wave upon turning on the THz light source 1 and a plurality of items of second image data obtained by picking up the measured wave upon turning off the THz light source 1 to produce a plurality of items of acquired first image data and a plurality of items of acquired second image data, and a data transferring unit 48 for transferring the plurality of items of acquired first image data and the plurality of items of acquired second image data to the external storage and processing device 9 as the digital data 8 with the identifying number for identifying the frame in which the image data is acquired attached every frame.

The identifying number in the exemplary embodiment of this invention makes a principal objective to determine whether the image data is acquired in the frame when the THz light source 1 turns on or in the frame when the THz light source 1 turns off. It will be assumed that the sensor synchronous signal 5 of the THz sensor 42 has a frequency of $F_S$, the light source control signal 6 has a frequency of $F_L$, and the dividing number n is equal to a ratio ($F_S/F_L$) of $F_S$ to $F_L$. In this event, the data transferring unit 48 of the THz camera 4 transfers, to the external storage and processing device 9, the identifying number which cyclically changes in a state where there is an upper limit of the dividing number n.

In other words, when the identifying number has a maximum number and a minimum number which are equal to $N_{max}$ and $N_{min}$, respectively, $N_{max}$, $N_{min}$, $F_S$, and $F_L$ are satisfied with the following expression:

$$1 \le (N_{max} - N_{min}) \le (F_S/F_L).$$

Figure 7:
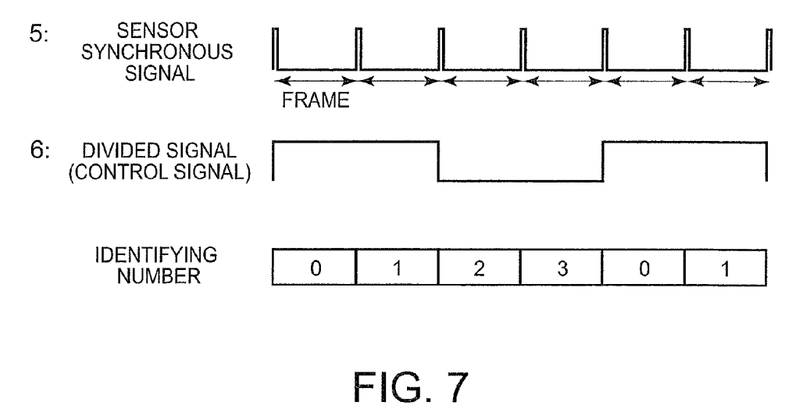
FIG. 7 is a view for use in describing relationship among a sensor synchronous signal, a light source control signal (a divided signal), and identifying numbers of frames included in digital data that are used in the lock-in image pickup system illustrated in FIG. 5.

FIG. 7 shows an example (a case of n=4) of relationship among the sensor synchronous signal 5, the light source control signal 6, and the identifying numbers of the frames which are transferred to the external storage and processing device 9 as the digital data 8 in the exemplary embodiment of this invention in a case where the frame is incrementally counted from a start of the picking-up. In the example being illustrated, the identifying number repeats a change so as to increase from 0 to 3 one by one and to return to 0 at the next frame.

The frequency divider 44 of the THz camera 4 supplies the THz light source 1 with the light source control signal 6 so that the light source control signal 6 takes ON (the logic "H" level) during the identifying number is equal to 0 and 1 and the light source control signal 6 takes OFF (a logic "L" level) during the identifying number is equal to 2 and 3.

Under the circumstances, a plurality of items of first image data having the identifying numbers of 0 and 1 are acquired in the frames at the THz light source 1 turns on while a plurality of items of second image data having the identifying numbers of 2 and 3 are acquired in the frames at the THz light source 1 turns off. Accordingly, on carrying out data processing in the external storage and processing device 9, by identifying the identifying number, it is possible to improve the image quality by certainly determining whether the image data (the digital data) 8 in the plurality of frames are the plurality of items of first image data of the frames at times when the THz light source 1 turns on or the plurality of items of second image data of the frames at times when the THz light source tunes off.

Figure 8:
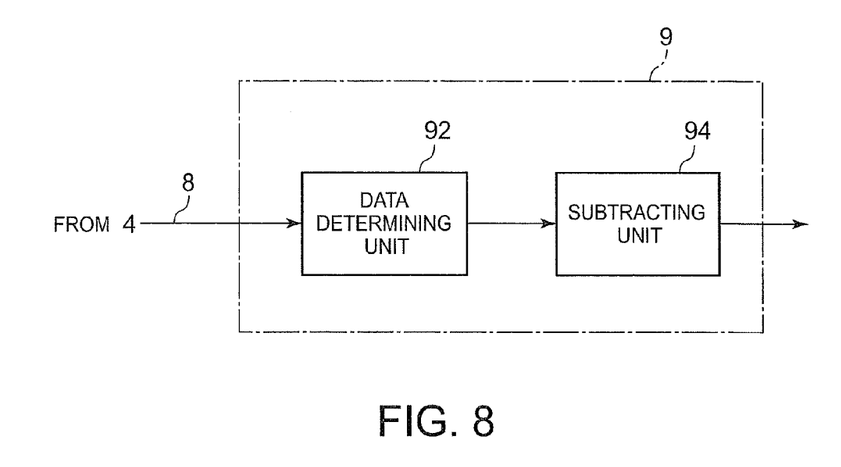
FIG. 8 is a block diagram of an external storage and processing device for use in the lock-in image pickup system illustrated in FIG. 5.

That is, the external storage and processing device 9 includes a data determining unit 92 for determining, on the basis of the identifying number, whether each frame of the digital data 8 is an item of the first image data or an item of the second image data to produce a plurality of items of determined first image data and a plurality of items of determined second image data, as shown in FIG. 8.

Although the description is made in a case where the identifying numbers of 0 and 1 correspond to the turning-on of the THz light source 1 and the identifying numbers of 2 and 3 correspond to the turning-off of the THz light source 1, the THz camera 4 may generate the light source control signal 6 so that the identifying numbers of 0 and 1 correspond to the turning-off of the THz light source 1 and the identifying numbers of 2 and 3 correspond to the turning-on of the THz light source 1.

Although the THz camera 4 may generate the light source control signal 6 in rules such as the identifying numbers of 1 and 2 correspond to the turning-on of the THz light source 1, the identifying numbers of 2 and 3 correspond to turning-on of the THz light source 1, or the like, it is preferable to assign the identifying numbers of 0 and 1 and the identifying numbers of 2 and 4 to the same polarity (ON or OFF), respectively. This is because the THz camera 4 can generate the light source control signal 6 by producing a most significant bit signal in the identifying number as it is (or with a state of simply inverting it).

In a case of n=4, although the identifying number may be assigned with 1 to 4 as a substitute for 0 to 3, it is preferable to assign the identifying number with 0 to 3. This is because the THz camera 4 can generate the light source control signal 6 by producing a most significant bit signal in the identifying numbers as it is (or with a state of simply inverting it).

The identifying number of the frame is generally assigned by simply counting up. In this event, the identifying number is assigned from a timing when the identifying number is reset to zero at an internal timing on starting the camera. However, inasmuch as a fixed time interval takes for acquiring stable image data from the THz camera 4, it is impossible to certainly discriminate between the image data of the frame upon turning on the THz light source 1 and the image data of the frame upon turning off the THz light source 1 on the basis of the identifying number alone.

In comparison with this, in the exemplary embodiment of this invention, the identifying number roundly changes and the identifying number is uniquely matched off against the turning-on/off of the THz light source 1. As a result, although the fixed time interval elapses after starting the camera, it is possible to certainly discriminate, on the basis of the identifying number, between the image data of the frame upon turning on the THz light source 1 and the image data of the frame upon turning off the THz light source 1 and it is possible to improve the image quality.

Now, the description will proceed to the structure of the digital data 8 transferred to the external storage and processing device 9. It is desirable that the digital data 8 have the structure so that the identifying number is transferred to the external storage and processing device 9 prior to the image data. This is because, although the situation where the digital data is correctively transferred due to any interference such as noises or the like may occur, inasmuch as the identifying number used is preliminarily known in the exemplary embodiment of this invention, if the identifying number other than them is read out, it is possible to take measures so as to omit the image data with the identifying number in question from processing. In comparison with this, in the case where the identifying number for the frame is simply assigned by counting up, it is impossible to take such measures because the identifying number is not limited.

Figure 9:
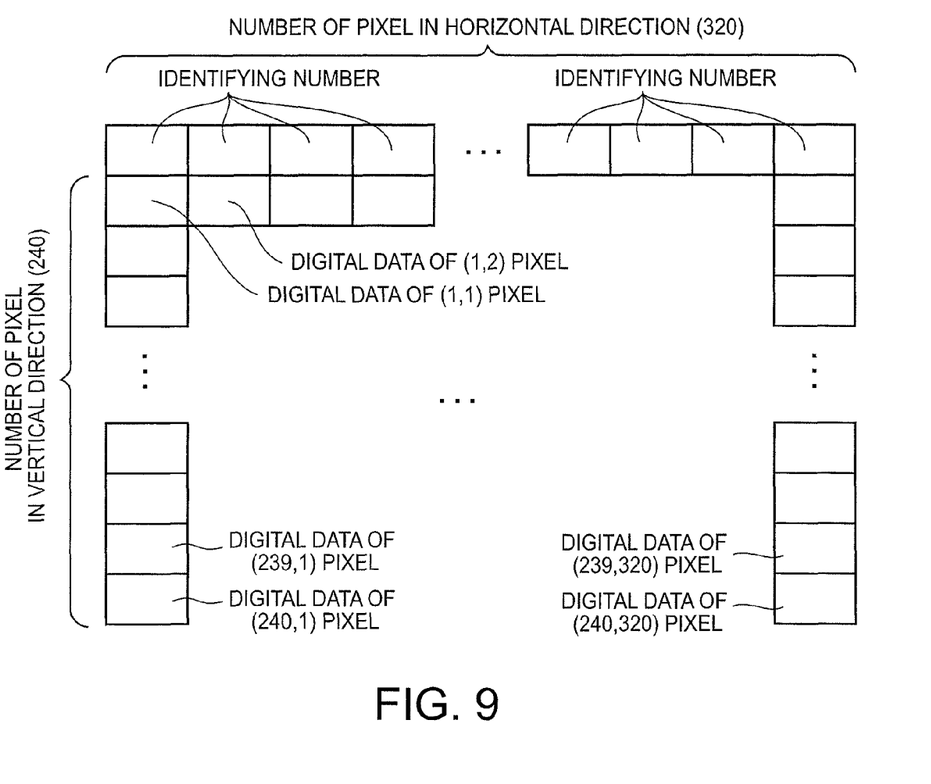
FIG. 9 is a view for use in describing an example of structure of digital data transferred to an external storage and processing device used in the lock-in image pickup system illustrated in FIG. 5.

In addition, in terms of the way to fight the noise, it is desirable to improve reliability of reading-out of the indentifying number by transferring the identifying number plural times instead of only once. For example, it is assumed that the camera picks up an image of (320×240) pixels. In this event, the identifying number may be added to all elements of a first row by setting data structure into (320×241), as shown in FIG. 9. Inasmuch as such data structure is data structure where not merely reliability of the reading-out of the identifying number is improved but also pixels of one row component are apparently increased, it is convenient for data processing in the external storage and processing device 9. Furthermore, in this event, it is possible to confirm the reliability of the digital data 8 transferred to the external storage and processing device 9 on the basis of a recognition ratio (the ratio of a count where the same identifying number is read out to 320) of the identifying number. It is a normal state in a case where the recognition ratio of 100% or the recognition ratio of 319/320 badly is obtained.

The external storage and processing device 9 comprises a subtracting unit 94 for subtracting the plurality of items of determined second image data from the plurality of items of determined first image data to produce difference image data, as shown in FIG. 8.

Now, the description will proceed to effects of the image pickup system according to the exemplary embodiment of the present invention.

A first effect is that it is possible to improve image quality by certainly discriminate against image data of a plurality of frames between the plurality of items of first image data of the frames upon tuning on the THz light source 1 and the plurality of items of second image data of the frames upon tuning off the THz light source 1.

This is because the THz camera 4 itself generates the light source control signal 6, the digital data 8 transferred from the THz camera 4 to the external storage and processing device 8 is given with the indentifying number of the frame as well as the image data, and the identifying number roundly changes on the basis of the ratio ($F_S/F_L$) of the frequency $F_S$ of the sensor synchronous signal 5 to the frequency $F_L$ of the light source control signal 6.

A second effect is that it is possible to improve image quality by certainly omitting, from average operation, the image data corresponding to the frames immediately after switching from the turning-on of the THz light source 1 to the turning-off of the THz light source 1 or switching from the turning-off of the THz light source 1 to the turning-on of the THz light source 1.

This is because, in the manner similar to the first effect, the THz camera 4 itself generates the light source control signal 6, the digital data 8 transferred from the THz camera 4 to the external storage and processing device 8 is given with the indentifying number of the frame as well as the image data, and the identifying number cyclically changes on the basis of the ratio ($F_S/F_L$) of the frequency $F_S$ of the sensor synchronous signal 5 to the frequency $F_L$ of the light source control signal 6.

A third effect is that it is possible to certainly acquire the identifying number of the frame without a mistake.

This is because on transferring the digital data 8 to the external storage and processing device 9, the digital data 8 includes the image data picked up by the THz camera 4 and the identifying number for identifying the frame in which the image data in question is acquired, and the indentifying number is transferred to the external storage and processing device 9 twice or more prior to the image data in question.

Example 1

Now, the description will proceed to a first example of the present invention.

Referring to FIG. 5, the lock-in image pickup system according to the first example of this invention uses, as the THz light source 1, a quantum cascade laser (QCL) for radiating an emission line (the THz wave) 2 having a frequency of 3.1 THz. The pulse control signal 7 has a pulse width of 300 nsec and a repetition frequency of 1 kHz. The sensor synchronous signal 5 of the THz camera 4 has a frequency of 60 Hz. The light source control signal 6 is a signal obtained by frequency dividing the sensor synchronous signal 5 on the basis of the dividing number of 16. Therefore, the light source control signal 6 has a frequency of 3.75 Hz and a duty factor of 50%. The present co-inventors carried out an experiment by supplying a light-emission driving circuit (not shown) of the QCL 1 with the control signal obtained by ANDing the light source control signal 6 and the pulse control signal 7.

In the first example, the image acquisition unit 46 of the THz camera 4 acquires eight items of first image data having a frame rate of 60 Hz for the duration (133.3 msec) of turning-on of the THz light source (QCL) 1 and eight items of second image data having the frame rate of 60 Hz for the duration (133.3 msec) of turning-off of the THz light source (QCL) 1. In the example being illustrated, the THz camera 4 comprises a THz array sensor as the THz sensor 42 as shown in FIG. 6.

The data transferring unit 48 of the THz camera 4 transfers, to the external storage and processing device 9, the digital data 8 obtained by adding identifying numbers of 0 to 15 for identifying frames in which the first and the second image data are acquired to the eight items of first image data and the eight items of second image data. The external storage and processing device 9 carries out a lock-in operation on the digital data 8. It is assumed that (image data)_m represents image data to which the identifying number of m (m=0, 1, . . . , and 15) is added. In this event, the lock-in operation is defined by the following Expression 1.

$$\left( \sum_{m=1}^{7} (\text{image data})\_m - \sum_{m=0}^{15} (\text{image data})\_m \right) \bigg/ 14 \qquad \text{(Expression 1)}$$

The reason why image data with the identifying numbers m of 0 and 8 are omitted is as follows. Inasmuch as the THz array sensor 42 has a time constant of 16 msec, it takes into consideration that signals of initial frames for the duration of turning-on and turning-off of the THz light source 1 do not sufficiently rise or fall.

Referring to FIGS. 10, 11A, 11B, and 12, the description will proceed to an example in which a signal-to-noise ratio is improved by twice to thrice as compared with the related art by applying the first example of the present invention.

Figure 10:
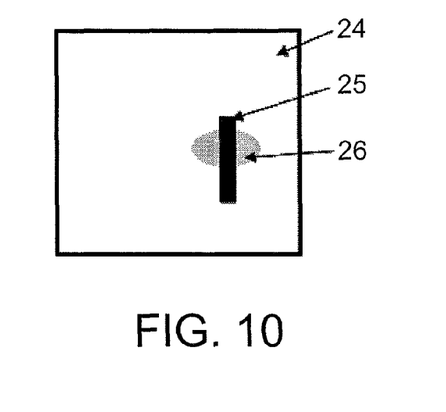
FIG. 10 is a view for use in describing a sample (a measured target) use in a lock-in image pickup system according to a first example of this invention.

As shown in FIG. 10, the present co-inventors prepared, as the measured target (sample) 3, an object in which a black cloth tape 25 is affixed on a reflection plate 24 on which an Al tape is affixed, radiated from the QCL (the THz light source) 1 cooled by liquid nitrogen the emission line (the THz wave) 2 having the frequency of 3.1 THz to a partial area 26 of the reflection plate 24, and picked up a reflected image by means of the THz camera 4 mounting the THz array sensor 42 having the number of pixels of (320×240) with a pixel pitch of 23.5 μm.

Figure 11A:
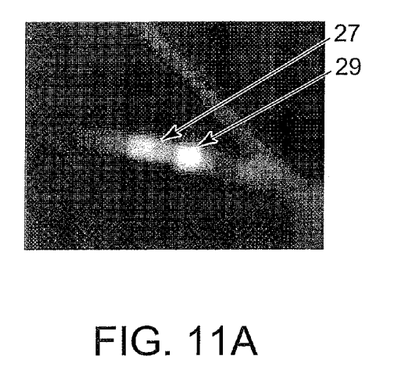
FIGS. 11A and 11B are views showing a difference image obtained by subtracting an integrated image of frames for the duration of turning-off of a THz light source from an integrated image of frames for the duration of turning-on of the THz light source regarding to the sample of FIG. 10 by using the lock-in image pickup system according to the first example of this invention.
Figure 11B:
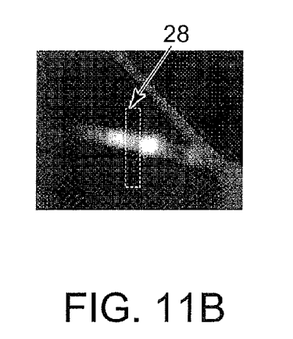

FIGS. 11A and 11B are views showing the reflected image (a long slender part in the vicinity of a center) of the emission line (the THz wave) 2 of the QCL 1 from the reflection plate 24. A long slender shape is for aberration of an off-axis parabolic mirror (not shown) used in the THz light source 1. It is possible to recognize a low intensity part 27 in the vicinity of a center of the long slender shape due to a low reflection factor of the above-mentioned black cloth tape 25, as shown in FIG. 11A. The low intensity part 27 corresponds to a position 28 of the above-mentioned black cloth tape 25, as shown in FIG. 11B.

The image of FIGS. 11A and 11B is an image obtained by carrying out the lock-in operation according to the above-mentioned Expression 1 and by integrating data of pixels of (24×24) for further increasing the signal-to-noise ratio. In the image of the QCL 1 of FIG. 11A, a high intensity part 29 at a right side has a signal-to-noise ratio of about 380.

Figure 12:
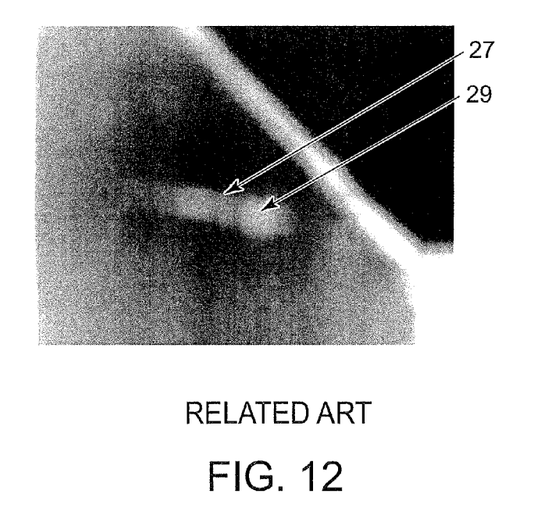
FIG. 12 is a view showing a difference image which is obtained by subtracting an image of a frame for the duration of turning-off of a THz light source from an image of a frame for the duration of turning-on of the THz light source regarding to the sample of FIG. 10 by using the lock-in image pickup system according to the first example of this invention and which corresponds to an image obtained by reproducing a function of the related lock-in image pickup system.

FIG. 12 is a view showing a difference image obtained by using one item of image data for the duration of turning-on of the THz light source and one item of image data for the duration of turning-ff of the THz light source in order to ascertain how mach is the signal-to-noise ratio improved in the first example of the present invention as compared with the related art. The sample is an object similar to that on acquiring the image of FIGS. 11A and 11B.

The image from the QCL 1 in FIG. 12 also has a shape similar to that in FIGS. 11A and 11B. The image of FIG. 12 also shows a result obtained by integrating the pixels of (24× 24). In the image of the QCL 1 of FIG. 12, a high intensity part 29 at a right side has a signal-to-noise ratio of about 130. In the manner which is described above, by using the first example of this invention, it is understood that it is possible to improve the signal-to-noise ratio about twice to thrice as compared with the related art.

While the invention has been particularly shown and described with reference to exemplary embodiments thereof, the invention is not limited to these embodiments. It will be understood by those of ordinary skilled in the art that various changes in form and details may be made therein without departing from the sprit and scope of the present invention as defined by the claims.

For example, although seven items of image data are used in the first example, all of image data may be used (the image of m=0 may be used in the Expression 1) if the THz array sensor 42 has a rapid time constant. Although the image of the sample (the measured target) 3 is acquired in the arrangement of reflection in the first example, the image may be acquired in an arrangement of transmission. Although the first example intends for the electromagnetic wave of the THz frequency band, this invention is not an art limited to the THz frequency band and can be applied to an electromagnetic wave of another frequency band such as infrared.

Furthermore, it is assumed that one period for the identifying numbers is called a phase. Under the circumstances, it may have a try at improvement of image quality by acquiring a plurality of phases of image data and by carrying out the lock-in operation. It is presumed that an image data with the identifying number of m at an i-th phase is defined by (image data)_i,m. Under the circumstances, the lock-in operation against the plurality of phases is defined by the following Expression 2:

$$\left(\sum_{i=1}^{k}\sum_{m=1}^{7}(\text{image data})\_i, m - \sum_{i=1}^{k}\sum_{m=9}^{15}(\text{image data})\_i, m\right)/14/k \quad \text{(Expression 2)}$$

In the Expression 2, k may be any natural number. Although an upper limit to k changes in dependence on a noise characteristic (whether random noises are dominant or not) of the image data or data capacity in which the external storage and processing device 9 can deal with, it is sufficient that the upper limit to k is set to about 100 to 1,000 as a guide.

What is claimed is:

1. An image pickup system comprising:
    a light source radiating an electromagnetic wave;
    a camera picking up a measured wave into which the electromagnetic wave transmits a measured target or reflects from the measured target to obtain image data comprising a plurality of frames; and
    an external storage and processing device connected to said camera,
    wherein said camera comprises:
        a light source control unit generating a light source control signal for controlling said light source to turn said light source on and off;
        an image acquisition unit acquiring first image data comprising a plurality of frames obtained by picking up the measured wave upon turning on said light source and second image data comprising a plurality of frames obtained by picking up the measured wave upon turning off said light source to produce acquired first image data acquired in plural consecutive frames when said light source is turned on and acquired second image data acquired in plural consecutive frames when said light source is turned off; and
        a data transferring unit transferring the acquired first image data and the acquired second image data to said external storage and processing device as digital data with an identifying number for identifying a frame in which the image data is acquired attached every frame,
    wherein said external storage and processing device comprises:
        a data determining unit determining, on the basis of the identifying number, whether each frame of the digital data is a frame of the first image data or a frame of the second image data to produce determined first image data determined in plural consecutive frames when said light source is turned on and determined second image data determined in plural consecutive frames when said light source is turned off; and
        a subtracting unit subtracting the determined second image data from the determined first image data to produce difference image data.

2. The image pickup system as claimed in claim 1, wherein the identifying number cyclically changes at a predetermined period.

3. The image pickup system as claimed in claim 2, wherein the identifying number has a maximum number of $N_{max}$ and a minimum number of $N_{min}$, said camera has a synchronous signal having a frequency of $F_S$, and the light source control signal has a frequency of $F_L$,
    wherein $N_{max}$, $N_{min}$, $F_S$, and $F_L$ are satisfied with a following expression:

$$1 \le (N_{max} - N_{min}) \le (F_S/F_L).$$

4. The image pickup system as claimed in claim 1,
    wherein said data transferring unit transfers the identifying number for identifying the corresponding frame twice or more prior to transferring the digital data every frame,
    wherein said data determining unit determines the identifying number by reading out the identifying number twice or more in one frame.

5. The image pickup system as claimed in claim 1, wherein the electromagnetic wave comprises a THz wave.

6. An image picking-up method for an image pickup system comprising a light source radiating an electromagnetic wave, a camera picking up a measured wave into which the electromagnetic wave transmits a measured target or reflects from the measured target to obtain image data comprising a plurality of frames, and an external storage and processing device connected to said camera, wherein said image picking-up method comprises:
    generating, from said camera, a light source control signal for controlling said light source to turn said light source on and off;
    acquiring, in said camera, first image data comprising a plurality of frames obtained by picking up the measured wave upon turning on said light source and second image data comprising a plurality of frames obtained by picking up the measured wave upon turning off said light source to produce acquired first image data acquired in plural consecutive frames when said light source is turned on and acquired second image data acquired in plural consecutive frames when said light source is turned off;
    transferring, from said camera, the acquired first image data and the acquired second image data to said external storage and processing device as digital data with an identifying number for identifying a frame in which the image data is acquired attached every frame;

determining, in said external storage and processing device, whether each frame of the digital data is a frame of the first image data or a frame of the second image data on the basis of the identifying number to produce determined first image data determined in plural consecutive frames when said light source is turned on and determined second image data determined in plural consecutive frames when said light source is turned off; and subtracting, in said external storage and processing device, the determined second image data from the determined first image data to produce difference image data.

7. The image picking-up method as claimed in claim 6, wherein the identifying number cyclically changes at a predetermined period.

8. The image picking-up method as claimed in claim 7, wherein the identifying number has a maximum number of $N_{max}$ and a minimum number of $N_{min}$, said camera has a synchronous signal having a frequency of $F_S$, and the light source control signal has a frequency of $F_L$, wherein $N_{max}$, $N_{min}$, $F_S$, and $F_L$ are satisfied with a following expression:

$$1 \leq (N_{max} - N_{min}) \leq (F_S/F_L).$$

9. The image picking-up method as claimed in claim 6, wherein said transferring transfers the identifying number for identifying the corresponding frame twice or more prior to transferring the digital data every frame, wherein said determining determines the identifying number by reading out the identifying number twice or more in one frame.

10. The image picking-up method as claimed in claim 6, wherein the electromagnetic wave comprises a THz wave.

* * * * *